United States Patent
Wang et al.

(10) Patent No.: US 7,622,106 B1
(45) Date of Patent: Nov. 24, 2009

(54) NECROSIS ASSAY

(75) Inventors: Xiaodong Wang, Dallas, TX (US); Sudan He, Dallas, TX (US); Lai Wang, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 12/399,872

(22) Filed: Mar. 6, 2009

(51) Int. Cl.
  *A61K 38/19* (2006.01)
  *C12P 21/00* (2006.01)
  *G01N 33/53* (2006.01)
  *C12N 5/00* (2006.01)

(52) U.S. Cl. ............... 424/85.1; 435/70.1; 435/7.1; 435/287.1; 435/325

(58) Field of Classification Search .............. None
  See application file for complete search history.

(56) References Cited

U.S. PATENT DOCUMENTS 7,309,792 B2 * 12/2007 Harran et al. ............... 548/237

OTHER PUBLICATIONS

He et al. (2009), Receptor Interacting Protein Kinase-3 Determines Cellular Necrotic Response to TNF-α, Cell, vol. 137, pp. 1100-1111.*
Petersen et al. (2007), Autocrine TNF-α,Signaling Renders Human Cancer Cells Susceptible to Smac-Mimetic-Induced Apoptosis, Cancer Cell, vol. 12, pp. 445-456.*
Li et al. (2004), A Small Molecule Smac Mimic Potentiates TRAIL- and TNF-α-Mediated Cell Death, Science, vol. 305, pp. 1471-1474.*

* cited by examiner

*Primary Examiner*—Christine J Saoud
*Assistant Examiner*—Jegatheesan Seharaseyon
(74) *Attorney, Agent, or Firm*—Richard Aron Osman

(57) ABSTRACT

A necrosis assays is performed with a cell expressing RIPK1 and RIP3 by (a) culturing the cell with a smac mimetic, caspase-8 inhibitor and TNF-α; and (b) detecting a resultant necrosis of the cell.

8 Claims, No Drawings

NECROSIS ASSAY

This invention was made with government support under Grant Number PO1 CA 95471 awarded by the National Cancer Institute (NCI). The government has certain rights in the invention.

The field of the invention is cell-based necrosis assays.

INTRODUCTION

Programmed cell death is executed through specific intracellular biochemical pathways. Apoptosis and necrosis are two common forms of programmed cell death that play essential roles in development and maintaining homeostasis in metazoan animals (Degterev and Yuan, 2008; Festjens et al., 2006). Defects in apoptosis and necrosis have been implicated in the etiology of many forms of human diseases (Lockshin and Zakeri, 2007).

Apoptosis is executed by a group of intracellular cysteine proteases, namely caspases (Yuan et al., 1993; Thornberry and Lazebnik, 1998). Upon caspase activation and subsequent cleavage of intracellular substrates, cells break into small membrane-wrapped vesicles known as apoptotic bodies (Kerr et al., 1972). Necrosis, on the other hand, is associated with organelle swelling, cytoplasmic membrane breakdown, and ensuing inflammation responses (Festjes et al., 2006).

Caspase activation during apoptosis is accomplished through two well-characterized pathways. The extrinsic pathway is activated through the binding of various death-inducing cytokines including TNF-α, TRAIL, and CD95 to their respective receptors leading to the activation of caspase-8 (Nagata, 1997; Peter and Krammer, 2003; Ashkenazi and Dixit, 1999); The intrinsic pathway is activated after mitochondrial intermembrane space proteins such as cytochrome c and Smac/Diablo are released into the cytosol where they activate caspase-9 and relieve inhibition imposed by the Inhibitors of apoptosis proteins (IAPs), respectively (Daniel and Korsmeyer 2004; Li et al., 1997, Du et al., 2000, Verhagen et al., 2000). Activated caspase-8 and caspase-9 subsequently cleave and activate several downstream caspases, including caspase-3 and caspase-7, which then cleave intracellular substrates, resulting in apoptosis.

These two pathways can cross talk through defined protein networks. The extrinsic apoptotic signal can be amplified by the intrinsic pathway via the cleavage of Bid by caspase-8 (Li et al., 1998; Luo et al., 1998). The truncated Bid, tBid, moves from the cytosol to mitochondria and causes the release of apoptogenic factors from mitochondria. On the other hand, Smac protein, once left mitochondria, induces the auto-degradation of cIAP1 and cIAP2, leading to activation of the noncanonical NF-κB pathway and formation of a RIPK1 containing-caspase-8 activating complex (Vince et al., 2007; Varfolomeev et al., 2007; Wang et al., 2008).

Interestingly, the same apoptosis-inducing cytokines, such as TNF-α, also cause necrosis in certain cell lines, especially when caspases are inhibited or cannot be activated efficiently (Laster et al., 1988; Grooten et al., 1993; Vercammen et al., 1997; Vercammen et al., 1998a; 1998b). In mouse fibrosarcoma L929 cells for example, TNF-α prominently causes necrosis instead of apoptosis. In human T cell leukemia Jurkat cells that are defective in caspase-8, activation of CD95 resulted in necrosis (Kawahara et al., 1998). The mechanism of TNF-α-induced necrotic cell death is not well understood, although mitochondrial dysfunction including generation of reactive oxygen species (ROS), inactivation of mitochondrial ADP/ATP exchange, and deregulation of Ca+ homeostasis have been implicated (Goossens et al., 1995; Lin et al., 2004; Temkin et al., 2006; Festjens et al., 2006).

One essential protein in TNF-α, TRAIL, and CD95-induced necrotic cell death is RIPK1 (Holler et al., 2000). RIPK1 is a multi-functional protein also known to mediate NF-κB and caspase-8 activation in response to TNF-α (Hsu et al., 1996; Kelliher et al., 1998; Petersen et al., 2007; Wang et al., 2008). Although the kinase activity of RIPK1 is not required for NF-κB activation, such activity is crucial for both caspase activation and necrosis induction (Holler et al., 2000; Wang et al., 2008).

The necrosis effector of RIPK1 is unknown. Neither is the relationship between RIPK1 kinase-dependent apoptosis and necrosis. Moreover, why certain cells such as L929 and Jurkat are able to undergo necrotic death in response to TNF-α family of cytokines while others only commit to apoptosis remains a mystery.

Our laboratory has been studying cellular apoptotic pathways using a small molecule that mimics the dimeric functional motif of Smac (Li et al., 2004). Our study revealed that the Smac mimetic together with TNF-α, promote the formation of a caspase-8-activating complex consisting of RIPK1, FADD, and caspase-8 (Petersen et al., 2007; Wang et al., 2008). During these studies, we noticed the Smac mimetic-induced cell death in human colon cancer HT-29 cells could not be blocked by pan-caspase inhibitors as in many other types of cells. Instead, they underwent massive necrosis. A systematic analysis of this form of necrosis using a combination of genome-wide siRNA screening and biochemical investigation revealed that a member of the receptor-interacting kinases, RIP3, is the key determinant for necrotic cell death downstream of RIPK1.

SUMMARY OF THE INVENTION

The invention provides necrosis assays and related methods and compositions. In one embodiment, the invention provides a method of inducing necrosis in a mammalian, preferably human cell expressing RIPK1 and RIP3, comprising the steps of: (a) culturing the cell with a smac mimetic, caspase-8 inhibitor and TNF-α; and (b) detecting a resultant necrosis of the cell.

In particular embodiments the method is practiced as a screen for modulators of necrosis, wherein: (i) the culturing step comprises contacting the cell with an agent, thereby biasing the resultant necrosis; (ii) the culturing step comprises contacting the cell with an agent, thereby inhibiting the resultant necrosis, and the detecting step identifies the agent as an inhibitor of necrosis; or (iii) the culturing step comprises contacting the cell with an agent, thereby inhibiting the resultant necrosis, the detecting step identifies the agent as an inhibitor of necrosis, and the method further comprising the step of confirming necrosis inhibitory activity of the agent in a mouse acute pancreatitis model.

In other embodiments, the TNF-α is autocrine, the RIP3 is ectopically expressed, the caspase-8 inhibitor is z-VAD or Q-VD-OPH, and/or the smac mimetic is a smac peptide or synthetic small molecule dimer.

In other embodiments, the invention provides necrosis assays specifically adapted to the subject methods and comprising the recited cell and a medium comprising the recited smac mimetic, caspase-8 inhibitor and TNF-α.

DESCRIPTION OF PARTICULAR EMBODIMENTS OF THE INVENTION

A subject necrosis assay method involves inducing necrosis in a cell expressing RIPK1 and RIP3, comprising the steps of: (a) culturing the cell with a smac mimetic, caspase-8 inhibitor and TNF-α; and (b) detecting a resultant necrosis of the cell. The assay method may be practiced as a screen for modulators (inhibitors or promoters) of necrosis, wherein but for the presence of a candidate agent (e.g. from a small molecule library) the method detects a reference or control necrosis, and that reference necrosis is compared with a test necrosis detected after exposure to the agent to identify the agent as a modulator of necrosis, which may be modulated in kind and/or degree (quantitatively and/or qualitatively), e.g. such as wherein (i) the culturing step comprises contacting the cell with an agent, thereby biasing the resultant necrosis (compared to negative control, e.g. an otherwise identical method in the absence of the agent). In such embodiments, the agent may be present in the culture medium with the smac mimetic, caspase-8 inhibitor and TNF-α, and/or pre-incubated with the cell prior to addition of the smac mimetic, caspase-8 inhibitor and TNF-α. In a particular embodiment, the screen is an assay for inhibitors of necrosis, wherein (ii) the culturing step comprises contacting the cell with an agent, thereby inhibiting the resultant necrosis, and the detecting step identifies the agent as an inhibitor of necrosis, the method optionally further comprising the step of confirming necrosis inhibitory activity of the agent in an animal model of necrosis, such as a mouse acute pancreatitis model.

The general assay is amenable to alternative variations. For examples, depending on the selected cell type, the TNF-α may be autocrine or provided exogenously, and the RIP3 may be naturally-expressed by the cell or ectopically expressed. Similarly, a wide variety of suitable the caspase-8 inhibitors known in the art may be used, such as z-VAD or Q-VD-OPH, and the smac mimetic may be a suitable smac peptide (e.g. U.S. Pat. Nos. 7,094,758; 7,041,784; 6,608,026; and 6,110,691) or preferably, a synthetic dimer such as described in U.S. Pat. No. 7,309,792 (see, also Li et al. 2004, Science 305, 1471-1474; and Wu et al. (Cell. 2007 Nov. 16; 131(4): 655-8) and references discussed therein). In a particular example, the dimer is a diyne of formula 3:

EXAMPLES

A Smac Mimetic Plus a Pan-Caspase Inhibitor Induce Necrosis in HT-29 Cells

Smac mimetics have been shown to induce apoptosis in certain tumor cell lines (Petersen et al., 2007; Vince et al., 2007; Varfolomeev et al., 2007), and death can be completely blocked with a pan-caspase inhibitor, z-VAD. Surprisingly, in HT-29 cells, exacerbated cell death occurred when cells were treated with Smac mimetic plus z-VAD or another pan-caspase inhibitor Q-VD-OPH. Consistent with previous reports, both cIAP1 and cIAP2 in HT-29 cells underwent accelerated degradation upon Smac mimetic treatment. Unlike apoptotic death, however, treated cells showed positive propidium iodide (PI) staining and cell death was prevented by a necrosis specific chemical inhibitor, Necrostatin-1 (Degterev et al., 2005).

To verify that cell death seen in HT-29 cells was indeed necrosis, cells treated with either vehicle DMSO, or Smac mimetic plus z-VAD, were analyzed by electron microscopy (EM). While most of DMSO treated cells showed normal cellular morphology including intact cytoplasmic membranes, a significant percentage of cells treated with Smac mimetic/z-VAD displayed swelled organelles including ER and mitochondria as well as discontinuous cytoplasmic membranes. No obvious apoptotic morphological changes were observed.

Smac Mimetic Plus z-VAD Induced Necrosis Requires TNF-α and RIPK1

Since Smac mimetic induces apoptosis in certain tumor lines as a result of autocrine TNF-α (Petersen et al., 2007; Vince et al., 2007; Varfolomeev et al., 2007), we checked whether autocrine TNF-α is required for the observed necrosis in HT-29 cells. Indeed, addition of a neutralizing anti-TNF-α antibody to the culture medium completely blocked this form of cell death. Consistently, knockdown of TNF receptor I also prevented these cells from dying. Moreover, exogenously added TNF-α augmented Smac mimetic plus z-VAD induced cell death and it did so in a dose dependent manner.

Since RIPK1 is a critical mediator for TNF-α induced necrosis (Holler et al., 2000), we also checked if the observed

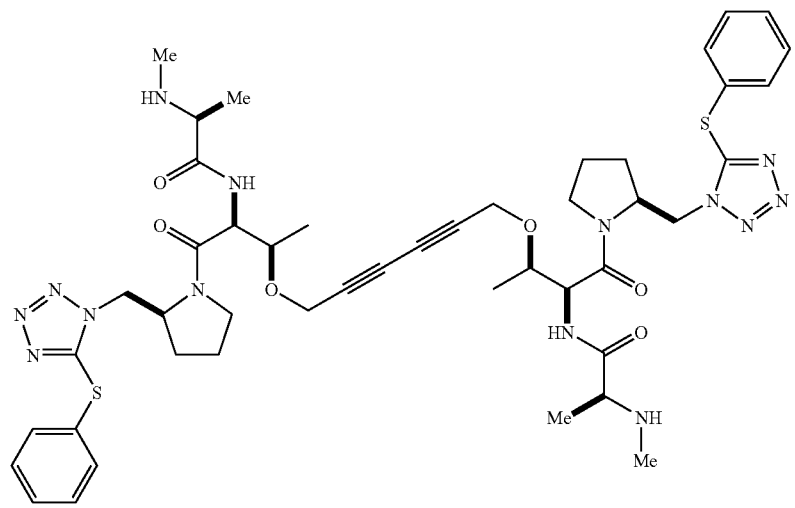

Smac mimetic-induced necrosis required RIPK1. Knockdown of RIPK1 almost completely blocked this form of cell death.

A Genome-Wide siRNA Screening Revealed RIP3 is Critical for Necrosis

The fact that Smac mimetic induced cell death requires both TNF-α and RIPK1 and that cell death was blocked by Necrostatin-1 indicated that such a form of cell death is similar to the previously described phenomenon of programmed necrosis or necropotosis (Holler et al., 2000; Lin et al., 2004; Degterev et al., 2008). The ability of Smac mimetic to drastically promote z-VAD and TNF-α induced necrosis, however, allowed us to further dissect the signaling pathway for necrosis.

We took advantage of this necrotic cell death model and performed a genome-wide siRNA screen using a Dharmacon human siRNA library consisting of 22,000 pools of four siRNA oligoes. Pools of siRNA were transfected into HT-29 cells cultured in 96-well plates, which were subsequently treated with TNF-α, Smac mimetic, and z-VAD. Exogenous TNF-α was added to increase the signal to noise ratio, and to rule out any siRNAs affecting TNF-α secretion. Cell viability was then measured and the ratio of viability between cells treated with these agents versus those treated with DMSO was scored. A siRNA oligo targeting RIPK1 was used as the positive control.

The screen came up with 72 hits defined such that when the targeted genes were knocked down; cell death was attenuated to a value of mean plus 5 standard deviation of the whole population (Table 1). The hit list includes kinases, ubiquitin E3 ligases, and other enzymes, signaling molecules, transcription factors, receptors as well as genes with unknown functions. As a validation to our screening strategy, the top hit with a score of 0.72 turned out to be RIPK1. The second best hit, with a score of 0.65, is another member of RIP kinase family, RIP3. RIP3 shares close similarity with RIPK1 at its N-terminal kinase domain and C-terminal RHIM domain through which it interacts with RIPK1 (Sun et al., 1999; 2002; Yu et al., 1999). Unlike RIPK1, RIP3 does not have the death domain at its C-terminus.

TABLE 1

Top 72 hits of RNAi screening.

| | Gene Symbol | Gene Name |
|---|---|---|
| Kinase(7) | RIPK1 | Receptor-interacting serine-threonine kinase 1 |
| | RIP3 | Receptor-interacting serine-threonine kinase 3 |
| | GNE | Glucosamine (UDP-N-acetyl)-2-epimerase/N-acetylmannosamine kinase |
| | CDKL5 | Cyclin-dependent kinase-like 5 |
| | GALK1 | Galactokinase 1 |
| | NME4 | nucleoside-diphosphate kinase 4 |
| | MGC45428 | Doublecortin and CaM kinase-like 2 |
| Other Enzyme(14) | PLA2G5 | Phospholipase A2, group V |
| | AMACR | Alpha-methylacyl-CoA racemase |
| | CNP | 2',3'-cyclic nucleotide 3' phosphodiesterase |
| | TCIRG1 | T-cell, immune regulator 1, ATPase, H+ transporting, lysosomal V0 protein a isoform 3 |
| | SIRT1 | Sirtuin (silent mating type information regulation 2 homolog) 1 (*S. cerevisiae*) |
| | MAN2C1 | Mannosidase, alpha, class 2C, member 1 |
| | LYZL4 | Lysozyme-like 4 |
| | MTMR2 | myotubularin-related protein 2 isoform 1 (putative tyrosine phosphatase) |
| | FKBP1B | FK506-binding protein 1B isoform a (cis-trans isomerase) |
| | TST | Thiosulfate sulfurtransferase (rhodanese) |
| | EBP | Emopamil binding protein (sterol isomerase) |
| | LOC388963 | similar to short-chain dehydrogenase/reductase 1 |
| | USP28 | Ubiquitin specific protease 28 |
| | CAPN9 | Calpain 9 |
| E3 Ligase(3) | CUL3 | Cullin 3 |
| | BARD1 | BRCA1 associated RING domain 1 |
| | CUL4B | Cullin 4B |
| Unknown Gene(9) | FLJ42486 | FLJ42486 protein |
| | NS5ATP13TP2 | NS5ATP13TP2 protein |
| | FLJ35728 | Hypothetical protein FLJ35728 |
| | C9ORF119 | Chromosome 9 open reading frame 119 |
| | DJ462O23.2 | Hypothetical protein dJ462O23.2 (NIPA-like domain containing 3 (NPAL3)) |
| | VAC14 | Vac14 homolog |
| | C7ORF7 | ankyrin repeat, SAM and basic leucine zipper domain containing 1 |
| | C14ORF10 | chromosome 14 open reading frame 10 |
| | LOC283585 | *Homo sapiens* hypothetical protein LOC283585 |
| Signaling Molecule(13) | NALP13 | NACHT, leucine rich repeat and PYD containing 13 |
| | RAB3D | RAB3D, member RAS oncogene family |
| | SOCS7 | suppressor of cytokine signaling 7 |
| | UNQ429 | Regenerating islet-derived 3 gamma |
| | EED | Embryonic ectoderm development (wd40 domain) |
| | DSPG3 | Dermatan sulfate proteoglycan 3 (*Homo sapiens* epiphycan (EPYC)) |
| | C20ORF136 | Sterile alpha motif domain containing 10 (sterile alpha motif domain containing 10 (SAMD10)) |
| | AIF1 | Allograft inflammatory factor 1 |

TABLE 1-continued

Top 72 hits of RNAi screening.

| | Gene Symbol | Gene Name |
|---|---|---|
| | LOC391248 | Similar to LPIN3 |
| | NPIP | Nuclear pore complex interacting protein |
| | BTBD2 | BTB (POZ) domain containing 2 |
| | RASGEF1B | RasGEF domain family, member 1B |
| | CHD3 | chromodomain helicase DNA binding protein 3 |
| Transcription Factor(13) | U11/U12 snRNP | U11/U12 snRNP 20K |
| | TRIM33 | Tripartite motif-containing 33 |
| | CREBL2 | CAMP responsive element binding protein-like 2 |
| | TFDP1 | Transcription factor Dp-1 |
| | P66ALPHA | GATA zinc finger domain containing 2A |
| | HES6 | Hairy and enhancer of split 6 (*Drosophila*) |
| | ZBTB33 | Zinc finger and BTB domain containing 33 |
| | TAL2 | T-cell acute lymphocytic leukemia 2 |
| | STAT1 | Signal transducer and activator of transcription 1, 91 kDa |
| | IRF2 | Interferon regulatory factor 2 |
| | MRPS12 | mitochondrial ribosomal protein S12 precursor |
| | EXOSC9 | exosome component 9 isoform 2 |
| | SNRPA | small nuclear ribonucleoprotein polypeptide A |
| Receptor(13) | OPRL1 | Opiate receptor-like 1 |
| | TACR2 | Tachykinin receptor 2 |
| | OR2C1 | Olfactory receptor, family 2, subfamily C, member 1 |
| | HLA-DQB2 | Major histocompatibility complex, class II, DQ beta 2 |
| | ITGAL | Integrin, alpha L (antigen CD11A (p180), lymphocyte function-associated antigen 1; alpha polypeptide) |
| | OR2W1 | Olfactory receptor, family 2, subfamily W, member 1 |
| | ITGB1BP2 | Integrin beta 1 binding protein (melusin) 2 |
| | LOC119764 | *Homo sapiens* olfactory receptor, family 4 |
| | SLC39A1 | Solute carrier family 39 (zinc transporter), member 1 |
| | RARG | Retinoic acid receptor, gamma |
| | CTGF | Connective tissue growth factor |
| | LOC389289 | *Homo sapiens* similar to annexin II receptor |
| | LIMS2 | G protein-coupled receptor 17 |

RIP3 and its Kinase Activity are Required for Necrosis but not Apoptosis

To verify the role of RIP3 in necrosis, a cell line that stably expresses a shRNA targeting RIP3 was generated from the parental HT-29 cells. Cto its parental cells, cells with RIP3 knockdown were resistant to necrosis. When RIP3 expression was restored with a shRNA resistant RIP3 transgene, cell death was re-established. However, if the transgene contains a K50A mutation known to abolish its kinase activity, cell death remained blocked. The difference in cell death in these different cells was not due to changes in RIPK1 since its level remained the same in all four cell lines.

We then tested whether RIP3 also has a role in apoptosis by measuring the cleavage of poly(ADP)ribose polymerase (PARP), a caspase-3/7 substrate, and cell survival rates between parental and RIP3 shRNA expressing HT-29 cells. No difference was seen in PARP cleavage or cell survival in these cells when apoptosis was induced by TNF-α plus Smac mimetic or cycloheximide. In addition to TNF-α, Trail and CD95/Fas have also been shown to be able to induce necrosis (Vercammen et al., 1997; 1998; Holler et al., 2001). To test whether RIP3 is also required for Trail and CD95-induced necrosis, we treated the same pair of parental and RIP3 shRNA expressing HT-29 cells with Trail/Smac mimetic/z-VAD or Fas ligand/Smac mimetic/z-VAD. Cell death induced by these agents was also completely eliminated in the RIP3 knockdown cells.

Ectopic Expression of RIP3 is Sufficient to Render Necrotic Response

To further confirm the role of RIP3 in TNF-α-induced necrosis, we treated 12 other cell lines with TNF-α, Smac mimetic, and z-VAD. We then measured cell viability and the level of RIP3 in these cell lines. Five other cell lines including human T cell leukemia Jurkat and CCRF-CEM cells, human monocytic leukemia U937 cells, mouse fibrosarcoma L929 cells, and mouse embryonic fibroblasts (MEFs) responded to the treatment and underwent necrosis. All these cell lines expressed RIP3. On the other hand, human cervical cancer HeLa cell, breast cancer MCF-7 cell, osteosarcoma U2OS cell, glioblastoma T98G cell, pancreatic cancer Panc-1 cell, non-small cell lung cancer NCI-460 and H2009 cells, as well as embryonic kidney 293T cells did not express any detectable RIP3 and they did not undergo cell death upon these treatments. Unlike RIP3, RIPK1 was ubiquitously expressed in all these cells.

TNF-α induced necrosis has been most extensively studied in mouse fibrosarcoma L929 cells due to its unique ability to undergo necrosis in response to TNF-α, or z-VAD alone (Grooten et al., 1993; Vercammen et al., 1998; Degterev et al., 2005; Kim et al., 2007). To test whether RIP3 is required for necrosis this L929 cells, we knocked down RIP3 with three individual mouse siRNA oligoes. Cell death induced by z-VAD, or TNF-α alone or combination of the two was attenuated when RIP3 was knocked down in L929 cells. The efficacy of necrosis blockage of these oligoes correlated perfectly with the efficiency of RIP3 knockdown. The levels of RIPK1 in L929 cells did not change after RIP3 was knocked down. Consistent with the idea that necrosis in L929 cells is executed by the same pathway as in HT-29 cells, the Smac mimetic also accelerated cell death in L929 cells in a concentration dependent manner.

Since cells resistant to TNF-α induced necrotic death are also defective in RIP3 expression, we then tested whether ectopic expression of RIP3 converts these cells to sensitive ones. When wild type RIP3 was expressed in T98G cells, we saw marked cell death in these cells upon necrosis induction compared to vector transfection controls. Expression of the kinase dead K50A mutant RIP3, however, did not cause cell death. Moreover, T98G cell death resulted from RIP3 expression was blocked by the necrosis inhibitor, Necrostatin-1. Similar effects were observed when RIP3 was expressed in HeLa cells, MCF-7 cells, and H2009 cells.

RIP3 Kinase-Dead Mutant Behaves as a Dominant Negative Regulator of Necrosis

To study how RIP3 induce necrosis, we first tested whether the kinase dead mutant of RIP3 functioned as a dominant negative mutant by stably expressing K50A mutant of RIP3 in HT-29 cells. Expression of RIP3 (K50A) at a level above the endogenous RIP3 blocked Smac mimetic/z-VAD or Smac mimetic/z-VAD plus TNF-α induced cell death.

To verify the blockage of cell death was indeed due to the dominant negative effect of RIP3 K50A mutant expression, we designed siRNA that specifically knocked down the mutant form of RIP3. Indeed, knockdown of this kinase dead form of RIP3 restored the cell death response as long as the endogenous RIP3 remained intact.

The dominant negative effect of RIP3 kinase dead mutant suggested that this protein might bind and sequester other signaling molecule in this necrosis pathway. The obvious candidate would be RIPK1. To test this directly, we immunoprecipitated RIP3 K50A from the HT-29 cells that stably expressed this transgene and the immune complex was analyzed by Western blotting using an anti-RIPK1 antibody. No RIPK1 was co-precipitated with the kinase dead RIP3 up to 8 hours of treatment with TNF-α alone, or TNF-α plus Smac mimetic or z-VAD. However, 4 hours after treatment of all three agents together, RIPK1 was found in the RIP3 K50A precipitate and the amount increased at 6 and 8 hours of treatment. The interaction between RIPK1 and RIP3 mutant was verified with reciprocal pull down with an anti-RIPK1 antibody. Again, the two proteins interacted only when all three necrosis inducing agents were present.

RIP3 Forms a Necrotic Complex with RIPK1

The dominant negative effect of kinase dead mutant RIP3 suggested that it might sequester RIPK1 and prevents its interaction with endogenous RIP3. To test whether endogenous RIP3 indeed interacts with RIPK1 upon necrosis induction, we treated HT-29 cells with TNF-α, Smac mimetic and z-VAD, followed by immuno-precipitation using an anti-RIPK1 antibody at different time points. Interestingly, an up-shift of RIP3 was observed after 4 hours of treatment and the shifted RIP3 continued to increase up to 8 hours. Correlating with the shift, RIP3 was found in the RIPK1 immuno-complex starting at 4 hours of necrosis induction and peaked at 8 hours. The up-shift of RIP3 and its interaction with RIPK1 only occurred under necrosis-inducing conditions. The observed up-shift of RIP3 is most likely due to phosphorylation that depends on its own kinase activity. No such shift was observed in RIP3 K50A mutant protein when it was pulled down with RIPK1. Moreover, the RIP3 band can be shifted down to the original position on SDS-PAGE gel with phosphatase treatment.

To further confirm the relevance of RIP3 up-shift and its induced interaction with RIPK1 to necrosis, HT-29 cells were co-treated with Necrostatin-1 during necrosis induction. Co-treatment with Necrostatin-1 completely prevented RIP3 up-shift as well as its interaction with RIPK1.

The importance of RIP3 and RIPK1 interaction for necrosis induction was verified with a mutation at the RHIM domain of RIP3 that is known to abolish its ability to interact with RIPK1 (Sun et al., 2002). Similar to the kinase dead mutant, introduction of this mutant protein was unable to render T98G cells responsiveness to the necrosis induction.

Since RIPK1 forms a complex with caspase-8/FADD upon treatment with TNF-α plus Smac mimetic and the complex is stabilized with z-VAD (Petersen et al., 2007; Wang et al., 2008), we wondered whether it is the same complex that recruits RIP3. To check that directly, we immuno-precipitated caspase-8 and analyzed the composition of the immuno-complex by Western blotting. RIP3 was found to associate with the RIPK-1/FADD/caspase-8 complex after 4 hours of treatment. RIP3 continued to be recruited to the complex for up to 6 hours of treatment. Much less proteins were immuno-precipitated at 8 hours with this anti-caspase-8 antibody. This observation might reflect that a large percentage of cells were dying. When cells were co-treated with Necrostatin-1, none of these complexes were able to form efficiently. This is consistent with the notion that Necrostatin-1 inhibits RIPK1 kinase activity, which is required for the formation of RIPK1/FADD/caspase-8 complex (Degterev et al., 2008; Wang et al., 2008).

To probe how RIP3 containing complex induces necrosis, we measured cellular localization of RIP3 in HT-29 cells before and after necrosis induction. RIP3 in resting cells is distributed in the cytosol. Upon necrosis induction, it forms punctuated and filamentary dots and rods reminiscent of some kinds of organelle staining. However, co-staining with intracellular organelle markers, including mitochondria, nuclei, ER, Golgi, lysosomes, endosomes, and peroxisomes, did not show obvious co-localization. It is therefore unlikely that the RIPK1/RIP3 necrosis complex simply destroys a cellular organelle by directly targeting it.

RIP3 Knock Out Mice Showed Less Tissue Damage in Mouse Acute Pancreatitis Model

The fact that RIP3 is a critical mediator of TNF-α-induced necrosis, yet is dispensable in animal development allowed us to investigate this form of cell death in RIP3 knockout mice (Newton et al., 2004). We reproduced RIP3 knockout mice as reported in Newton et al and studied its role under pathological conditions in which necrotic cell death has been implicated.

We first verified the importance of RIP3 in TNF-α-induced necrosis in embryonic fibroblasts (MEFs) prepared from embryos of RIP3−/+mating. MEFs from RIP3 knockout embryos did not contain any RIP3 protein while the heterozygote MEF had roughly half of the RIP3 as in the wild type. RIPK1 level did not change in these MEFs. When these MEFs were treated with necrosis inducing agents including TNF-α/Smac mimetic/z-VAD or TRAIL/Smac mimetic/z-VAD, MEFs from the wild type animal committed to death while cells from RIP3 knockout embryos did not. Consistently, macrophages isolated from wild type animal were sensitive to Smac mimetic/z-VAD or LPS plus z-VAD treatment while cells from RIP3 knockout mice were completely resistant. In contrast, no difference in apoptosis was seen in RIP3 wild type and knockout MEF when they were treated with TNF-α plus cycloheximide, an observation that agrees with what was reported in the original RIP3 knockout paper (Newton et al., 2004).

We chose cerulein-induced pancreatitis in mice to further study the role of RIP3 in this necrosis-associated disease model. Most cell death in the pancreas was found to be necrotic rather than apoptotic and the degree of necrosis correlates with severity of the disease (Mareninova et al., 2006). Interestingly, when we analyzed the expression of RIP3 in different tissues from the cerulein-treated animals, we noticed a dramatic increase of RIP3 protein in the pancreas. No such increase was seen in other tissues including liver, brain, spleen, and thymus. Twenty-four hours after the treatment, 8 out of 12 cerulein treated wild type animals showed multiple areas of pancreas acinar cell loss and necrosis. This effect was largely prevented in all RIP3 knockout littermates. Consistently, serum amylase was elevated to much higher levels in wild type animals 24 hours after treatment of cerulein compared to those in the RIP3 knock out littermates.

RIP3 Represents a Key Switch Point in TNF-α-Induced Cellular Necrotic Pathway

RIP3 had been an innocuous member of the RIP kinase family. Although ectopic expression of RIP3 in mammalian cells has been shown to cause apoptosis, such a phenotype could be the result of artificially high expression (Yu et al., 1999; Sun et al., 1999). Indeed, knockout of RIP3 in mice did not cause any measurable defect in development, fertility, NF-κB activation, and apoptosis response (Newton et al., 2004). In contrast, the founding member of the RIP family, RIPK1, has critical roles in the above mentioned signing pathways and RIPK1 knockout mice die soon after birth (Kelliher et al., 1998; Holler et al., 2000; Petersen et al., 2007; Wang et al., 2008).

The pro-apoptotic function of RIPK1 is to form a caspase-8 activation complex in response to TNF Receptor I activation (Wang et al., 2008). This process starts with the accelerated degradation of cIAP1/2 induced by Smac protein (or Smac mimetics), and proceeds with release of RIPK1 from the TNFRI, deubiquitination of RIPK1 by the deubiquitin enzyme CYLD, and subsequent recruitment of FADD and caspase-8 (Wang et al., 2008). The activation of caspase-8 in this complex results in cleavage of RIPK1 by caspase-8 (Lin et al., 1999). The cleavage of RIPK1 by caspase-8 terminates necrotic signal.

The work presented here indicated that RIP3 is also recruited to the RIPK1 complex through direct interaction between the RHIM domains of RIPK1 and RIP3. If caspase-8 is inhibited after death receptor activation, RIP3 forms a stable complex with RIPK1/FADD/caspase-8 and transforms it to a pro-necrosis complex. The necrosis blocker Necrostatin-1 efficiently prevents RIPK1/FADD/caspase-8 complex formation and subsequent recruitment of RIP3 to the complex. Thus, apoptosis and necrosis induced by death inducing cytokines share a common biochemical pathway down to the step of RIPK1 activation following receptor activation, cIAP1/2 degradation, and deubiquitination of RIPK1 by CYLD. It is thus not surprising that CYLD is required for efficient RIPK1/FADD/caspase-8 complex formation (Wang et al., 2008) and scored as the top hit in a genome-wise siRNA screen in L929 cells for genes whose knockdown prevented necrosis in these cells (Hitomi et al., 2008). It is likely that RIP3 is recruited to RIPK1 independent of binding of FADD and caspase-8 since it binds to RIPK1 through its RHIM domain while FADD binds RIPK1 at its C-terminal DD domain. If this is the case, the kinetics of RIP3 vs FADD/caspase-8 binding to RIPK1 could potentially determine the ratio of necrotic and apoptotic response of cells to these cytokines.

The status of NF-αB also seems to effect cellular necrotic response to TNF-α/Smac mimetic/z-VAD. Blockage of NF-κB with an IKK inhibitor enhanced necrosis in HT-29 cells treated with these agents.

Unlike RIPK1 that is ubiquitously expressed in all cells and tissues examined, the expression of RIP3 in different tissues and cell lines is variable. Only cells with RIP3 expression underwent necrosis upon addition of TNF-α, mac mimetic/z-VAD while cells without RIP3 all survived such treatment. Introducing exogenous RIP3 to several of these cell lines rendered them responsive to necrotic induction. RIP3, therefore, seems to be a specialized signaling protein for necrosis.

Mechanism of RIP3-Dependent Necrotic Cell Death

The recruitment of RIP3 to RIPK1 makes the complex pro-necrotic. Just like RIPK1, the kinase activity of RIP3 is critical for necrosis. In fact, the kinase dead RIP3 still binds to RIPK1 upon necrosis induction and dominant negatively blocks necrosis. It is clear that the kinase activities of both RIPK1 and RIP3 as well as their ability to interact with each other are required for induction of necrosis.

However, it remains puzzling how RIP3/RIPK1 complex induces necrosis. Since RIP3 does not co-localize with all the major cell organelles examined), it is unlikely that the RIP3/RIPK1 pro-necrotic complex directly destroy them. It is possible that this complex phosphorylates some specific cellular target(s) in a necrotic pathway. Identifying the unknown components of such a pathway should be an exciting topic for future studies.

Although not affected directly, mitochondria could be at least one of the targets in this pathway. Mitochondria are the center for energy production, Ca++ buffering, and ROS production. Malfunction of mitochondria will lead to collapse of the cell and thus necrosis. Indeed, in THP-1 cells, ANT, the mitochondrial ADP/ATP nucleotide exchanger, is locked into its cytosolic configuration and is unable to carry out ADP/ATP exchange when treated with TNF-α plus z-VAD (Temkin et al., 2006). Inactivation of ANT stops oxidative phosphorylation-mediated ATP generation, resulting in depletion of cellular energy pools and necrotic cell death. Mitochondrial cyclophilin D, the regulator of ANT, might be a target of necrosis inducers. Consistently, MEFs from cyclophilin D knock out mice are partially resistant to TNF-α, Smac mimetic plus z-VAD induced cell death, although the resistance is not as complete as the RIP3 knockout MEFs (Nakagawa et al., 2005; Baines et al., 2005).

Reactive oxygen species (ROS) have been implicated in TNF-α-induced, RIPK1-dependent necrosis (Lin et al. 2004). Nox1 NADPH oxidase has been shown to work downstream of RIPK1 to generate ROS in L929 and MEF cells (Kim et al., 2007). However, ROS dependence seems cell-type specific. ROS quenching prevented necrosis in L929 cells but failed to do so in HT-29 cells treated with TNF-α, Smac mimetic, and z-VAD. One possibility is that similar to the extrinsic apoptosis pathways that certain cells (type II) require mitochondria to amplify the cell death signal while others do not (Scaffidi, et al., 1998), necrotic signaling may need to be amplified through ROS in certain cells, but not in others.

Phospholipase A2 (PLA2) activation has also been shown to contribute to TNF-α induced necrosis, possibly by disruption of organelle and plasma membranes (Cauwels et al., 2003). It is not surprising that one of these enzymes, PLA2G5, scores a hit in our genome-wide siRNA screen. The effect of knocking down this gene on necrosis, however, was not as dramatic as RIP3 knockdown. Given the fact that knockdown efficiency varies among different siRNA for different genes and levels of proteins required for necrosis induction may differ as well, it will take a while to distinguish the true RIP3 downstream necrosis effectors from the false hits on the list (Hitomi et al., 2008). It is also possible that the downstream effectors of RIP3 are many, which contribute incrementally to necrotic death of cells in a way similar to cleavage of many caspase substrates during apoptosis. Sorting through these hits, in combination with biochemical analysis for RIP3 kinase substrates, may eventually lead to the understanding how cells are dismissed during TNF-α-mediated necrosis by the RIPK1/RIP3 necrosis-inducing complex.

Physiological and Pathological Significance of Necrotic Death

Necrosis has often been associated with extreme physical-chemical injury. Although TNF-α, CD95 ligand, or TRAIL induced death receptor activation has been well documented to cause necrosis in certain cells, the significance of necrosis remains to be validated under physiological and pathological situations.

The seemingly specific role of RIP3 in necrosis, and lack of obvious phenotype of RIP3 knockout mice under normal conditions provided a genetic system to study necrosis. We therefore tested the role of RIP3 in mouse models of cerulein-induced pancreatitis. In this case, RIP3 protein is elevated in the injured tissue, and mice without RIP3 are protected from tissue damage. Interestingly, although big differences between wild type and RIP3 knockout mice were observed 24 hours after the first cerulein injection, similar tissue damage was seen in these animals 10 hours after first cerulein injection, consistent with the idea that it is not the initial injury that is RIP3 dependent. More likely, the subsequent damage caused by the ensuing inflammatory response was eliminated in the pancreas of RIP3 knockout mice and the initial damage caused by the pancreatic digestive enzyme had recovered. These results suggest that RIP3-dependent necrosis is part of a defense system against tissue injury caused by physical or chemical damage, and maybe more frequently, by microbe infections. Necrotic death could be an important way to eliminate damaged cells especially when apoptosis cannot be activated efficiently or is blocked. Unlike apoptosis, necrosis may also amplify the initial damage signal by activating inflammatory response, which further destroys the damaged cells and facilitates the clean up of cell debris. Not surprisingly, RIP3 expresses strongly in immunologic organs like thymus and spleen and its expression is induced during tissues injury or following wounding (Adams et al., 2007).

Other systems in which morphologically defined necrosis occur include T lymphocytes after HIV-1 infection, neutrophils and macrophages after bacterial infection (Festjes et al., 2006). In these cases, viruses and bacteria often carry their own caspase inhibitors, and necrotic death may serve as an important defense mechanism to eliminate the microbes and solicit inflammation by releasing intracellular contents and/or cytokines. It is worth noting that RIP3 is not just functioning downstream of TNFRI and its related death receptors. Toll-like receptors (TLRs) also transduce their signals through RIPK1 and RIP3 (Meylan et al., 2004).

Necrosis, when run in excess, could potentially cause irreversible tissue damage and death of the whole animal. Therefore, inhibition of RIP3 mediated necrosis with chemical inhibitors has the possibility to treat acute or chronic inflammation-related diseases such as pancreatitis.

REFERENCES

Adams, S., Pankow, S., Werner, S., and Munz, B. (2007). Regulation of NF-B Activity and Keratinocyte Differentiation by the RIP4 Protein: Implications for Cutaneous Wound Repair. J. Inves. Derm. (2007) 127, 538-544.

Ashkenazi A, Dixit V M. (1999). Apoptosis control by death and decoy receptors. Curr. Opin. Cell Biol. 11, 255-260.

Baines, C. P., Kaiser, R. A., Purcell, N. H., Blair, N. S., Osinska, H., Hambleton, M. A., Brunskill, E. W., Sayen, M. R., Gottlieb, R. A., Dorn, G. W., Robbins, J., and Molkentin, J. D. (2005). Loss of cyclophilin D reveals a critical role for mitochondrial permeability transition in cell death. Nature 434, 658-662.

Cauwels, A., Janssen, B., Waeytens, A., Cuvelier, C., and Brouckaert, P. (2003). Caspase inhibition causes hyper-acute tumor necrosis factor-induced shock via oxidative stress and phospholipase A2. Nature Immunol. 4, 387-393.

Danial, N. N., and Korsmeyer, S J. (2004). Cell death: Critical control points. Cell 116, 205-219.

Degterev, A., Huang, Z., Boyce, M., Li, Y., Jagtap, P., Mizushima, N., Cuny, G. D., Mitchison, T. J., Moskowitz, M. A., and Yuan, J. (2005). Chemical inhibitor of nonapoptotic cell death with therapeutic potential for ischemic brain injury. Nat. Chem. Biol. 1, 112-119.

Degterev, A., Hitomi, J., Germscheid, M., Ch'en, I. L., Korkina, O., Teng, X., Abbott, D., Cuny, G. D., Yuan, C., Wagner, G., Hedrick, S. M., Gerber, S. A., Lugovskoy, A., and Yuan. J. (2008). Identification of RIP1 kinase as a specific cellular target of necrostatins. Nat. Chem. Biol. 4, 313-321.

Degterev, A, and Yuan, J. (2008). Expansion and evolution of cell death programmes. Nat. Rev. Mol. Cell Biol. 9, 378-390.

Du, C., Fang, M., Li, Y., and Wang, X. (2000). Smac, a mitochondrial protein that promotes cytochrome c-dependent caspase activation by eliminating IAP inhibition. Cell 102, 133-142.

Festjens, N., Vanden Berghe, T., and Vandenabeele, P. (2006). Necrosis, a well-orchestrated form of cell demise: Signalling cascades, important mediators and concomitant immune response. Biochimica. Et. Biophysica. Acta. 1757, 1371-1387.

Goossens, V., J. Grooten, K. De Vos, and W. Fiers. 1995. Direct evidence for tumor necrosis factor-induced mitochondrial reactive oxygen intermediates and their involvement in cytotoxicity. Proc. Natl. Acad. Sci. USA. 92: 8115-811

Grooten, J., Goossens, V., Vanhaesebroeck, B., and Fiers, W. (1993). Cell membrane permeabilization and cellular collapse, followed by loss of dehydrogenase activity: early events in tumour necrosis factor-induced cytotoxicity. Cytokine. 5, 546-555.

Hitomi, J., Christofferson, D. E., Ng, A., Yao, J., Degterev, A., Xavier, R. J., and Yuan, J. (2008). Identification of a Molecular Signaling Network that Regulates a Cellular Necrotic Cell Death Pathway. Cell 135, 1311-1323.

Hsu, H., Huang, J., Shu, H., Baichwal, V., and Goeddel, D. V. (1996).
TNF-dependent recruitment of the protein kinase RIP to the TNF receptor-1 signaling complex. Immunity 4, 387-396.

Holler, N., Zaru, R., Micheau, O., Thome, M., Attinger, A., Valitutti, S., Bodmer, J. L., Schneider, P., Seed, B., and Tschopp, J. (2000). Fas triggers an alternative, caspase-8-independent cell death pathway using the kinase RIP as effector molecule, Nat. Immunol. 1, 489-495.

Kawahara, A., Ohsawa, Y., Matsumura, H., Uchiyama, Y. and Nagata, S. (1998). Caspase-independent cell killing by Fas-associated protein with death domain. J. Cell Biol. 143, 1353-1360.

Kelliher. M. A., Grimm, S., Ishida, Y., Kuo, F., Stanger, B. Z., and Leder, P. (1998). The death domain kinase RIP mediates the TNF-induced NF-kappaB signal. Immunity 8, 297-303.

Kerr, J. F., Wyllie, A. H., and Currie, A. R. (1972). Apoptosis: a basic biological phenomenon with wide-ranging implications in tissue kinetics". Br. J. Cancer 26, 239-257.

Kim, Y-S., Morgan, M. J., Choksi, S., and Liu Z-G (2007). TNF-Induced Activation of the Nox1 NADPH Oxidase and Its Role in the Induction of Necrotic Cell Death. Mol. Cell 26, 675-687.

Laster, S. M., Wood, J. G., and Gooding, L. R. (1988). Tumor necrosis factor can induce both apoptotic and necrotic forms of cell lysis. J. Immunol. 141, 2629-2635.

Li, H., Zhu, H., Xu, C. J., and Yang, J. (1998). Cleavage of Bid by caspase-8 mediates the mitochondrial damage in the Fas pathway of apoptosis. Cell 94, 491-501.

Li, L., Thomas, R. M., Suzuki, H., De Brabander, J. K., Wang, X., and Harran, P. G. (2004). A small molecule Smac mimic potetiates TRAIL- and TNFalpha-mediated cell death. Science 305, 1471-1474.

Li, P., Nijhawan, D., Budihardjo, I., Srinivasula, S. M., Ahmad, M., Alnemri, E. S., and Wang, X. (1997). Cytochrome c and dATP-dependent formation of Apaf-1/caspase-9 complex initiates an apoptotic protease cascade Cell 91, 479-489

Lin, Y., Choksi, S., Shen, H. M., Yang, Q. F., Hur, G. M., Kim, Y. S., Tran, J. H., Nedospasov, S. A., and Liu, Z. G. (2004).

Tumor necrosis factor-induced nonapoptotic cell death requires receptor-interacting protein-mediated cellular Reactive oxygen species accumulation. J. Biol. Chem. 279, 10822-10828.

Lin, Y., Devin, A., Rodriguez, Y., and Liu, Z-G. (1999). Cleavage of the death domain kinase RIP by Caspase-8 prompts TNF-induced apoptosis. Genes and Dev. 13, 2514-2526.

Lockshin, R. A. and Zakeri, Z. (2007). Cell death in health and disease. J. Cell Mol. Med. 11, 1214-1224.

Luo, X., Budihardjo, I., Zou, H., Slaughter, C., ad Wang, X. (1998). Bid, a Bcl-2 interacting protein, mediates cytochrome c release from mitochondria in response to activation of cell surface death receptors. Cell 94, 481-490.

Mareninova, O. A., Sung, K., Hong, P., Lugea, A., Pandol, S. J., Gukovsky, I., and Gukovskayal A. S. (2006). Caspases protect from necrotizing pancreatitis. J. Biol. Chem. 281, 3370-3381.

Meylan, E., Burns, K., Hofmann, K., Blancheteau, V., Martinon, F., Kelliher, M., and Tschopp, J. (2004). RIP1 is an essential mediator of Toll-like receptor 3-induced NF-kappa B activation. Nat. Immunol. 5, 503-507

Newton, K., Sun, X., and Dixit, V. M. (2004). Kinase RIP3 is dispensable for normal NF-kappa Bs, signaling by the B-cell and T-cell receptors, tumor necrosis factor receptor 1, and Toll-like receptors 2 and 4. Mol. Cell Biol. 24, 1464-1469.

Peter, M. E., and Krammer, P. H. (2003). The CD95 (APO-1/Fas) DISC and beyond, Cell Death Differ. 10, 26-35.

Petersen, S. L., Wang, L., Yalcin-Chin, A., Li, L., Peyton, M., Minna, J., Harran, P., and Wang, X. (2007). Autocrine TNFalpha signaling renders human cancer cells susceptible to Smac-mimetic-induced apoptosis. Cancer Cell 12, 445-456.

Scaffidi, C., Fuida, S., Srinivasan, A., Friesen, C., Li, F., Tomaselli, K. J., Debatin, K. M., Krammer, P. H., and Peter, M. E. (1998). Two CD95 (Apo-1/Fas) signaling pathways. EMBO J. 17, 1675-1687.

Sun, X., Lee, J., Navas, T., Baldwin, D. T., Stewart, T. A., and Dixit, V. M. (1999). RIP3, a novel apoptosis-inducing kinase. J. Biol. Chem. 274, 16871-16875.

Sun, X., Yin, J., Starovasnik, M. A., Fairbrother, W. J., and Dixit, V. M. (2002). Identification of a novel homotypic interaction motif required for the phosphorylation of receptor-interacting protein (RIP) by RIP3. J. Biol. Chem. 277, 9505-9511.

Temkin V, Huang Q, Liu H, Osada H, Pope R M. (2006). Inhibition of ADP/ATP exchange in receptor-interacting protein-mediated necrosis. Mol. Cell Biol. 26, 2215-2225.

Thornberry, N. A., and Lazebnik, Y. (1998). Caspases: enemies within. Science 281, 1312-1316.

Varfolomeev, E., Blankenship, J. W., Wayson, S. M., Fedorova, A. V., Kayagaki, N., Garg, P., Zobel, K., Dynek, J. N., Elliott, L. O., Wallweber, H. J., Flygare, J. A., Fairbrother, W. J., Deshayes, K., Dixit, V. M., and Vucic. D. (2007). IAP antagonists induce autoubiquitination of c-IAPs, NF-kappaB activation, and TNFalpha-dependent apoptosis. Cell 131, 669-681.

Vercammen, D., Vandenabeele, P., Beyaert, R., Declercq, W., and Fiers, W. (1997). Tumour necrosis factor-induced necrosis versus anti-Fas-induced apoptosis in L929 cells, Cytokine 9, 801-808.

Vercammen, D., R. Beyaert, G. Denecker, V. Goossens, G. Van Loo, W. Declercq, J. Grooten, W. Fiers, and P. Vandenabeele. (1998a). Inhibition of caspases increases the sensitivity of L929 cells to necrosis mediated by tumor necrosis factor. J. Exp. Med. 187, 1477-1485

Vercammen, D., Brouckaert, G., Denecker, G., Van de Craen, M., Declercq, W., Fiers, W., and Vandenabeel, P. (1998). Dual signaling of the Fas receptor: initiation of both apoptotic and necrotic cell death pathways. J. Exp. Med. 188, 919-930.

Verhagen, A. M., Ekert, P. G., Pakusch, M., Silke, J., Connolly, L. M., Reid, G. E., Moritz, R. L., Simpson, R. J., and Vaux, D. L. (2000). Identification of DIABLO, a mammalian protein that promotes apoptosis by binding to and antagonizing IAP proteins. Cell 102, 43-53.

Vince, J. E., Wong, W. W., Khan, N., Feltham, R., Chau, D., Ahmed, A. U., Benetatos, C. A., Chunduru, S. K., Condon, S. M., McKinlay, M., Brink, R., Leverkus, M., Tergaonkar, V., Schneider, P., Callus, B. A., Koentgen, F., Vaux, D. L., and Silke, J. (2007). IAP antagonists target cIAP1 to induce TNFalpha-dependent apoptosis. Cell 131, 682-693.

Wang, L., Du, F., and Wang, X. (2008). TNF-alpha induces two distinct caspase-8 activation pathways. Cell 133, 693-703.

Yu, P. W., Huang, B. C., Shen, M., Quast, J., Chan, E., Xu, X., Nolan, G. P., Payan, D. G., and Luo, Y. (1999). Identification of RIP3, a RIP-like kinase that activates apoptosis and NFkappaB. Curr. Biol. 9, 539-542.

Yuan, J., Shaham, S., Ledoux, S., Ellis, H. M. and Horvitz, H. R. (1993). The C. elegans Cell Death Gene ced-3 Encodes a Protein Similar to Mammalian Interleukin-1☐☐-Converting Enzyme. Cell 75, 641-652.

Zhong, Q., Gao, W., Du, F., and Wang, X. (2005). Mule/ARF-BP1, a BH3-only E3 ubiquitin ligase, catalyzes the polyubiquitination of Mcl-1 and regulates apoptosis. Cell 121, 1085-1095.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

What is claimed is:

1. A method of inducing necrosis in a mammalian cell expressing RIPK1 and RIP3, comprising the steps of:
   (a) culturing the cell with a smac mimetic, caspase-8 inhibitor and TNF-α; and
   (b) detecting a resultant necrosis of the cell.

2. The method of claim 1, wherein the culturing step comprises contacting the cell with an agent, thereby biasing the resultant necrosis.

3. The method of claim 1, wherein the culturing step comprises contacting the cell with an agent, thereby inhibiting the resultant necrosis, and the detecting step identifies the agent as an inhibitor of necrosis.

4. The method of claim 1, wherein the culturing step comprises contacting the cell with an agent, thereby inhibiting the resultant necrosis, the detecting step identifies the agent as an inhibitor of necrosis, and the method further comprising the step of confirming necrosis inhibitory activity of the agent in a mouse acute pancreatitis model.

5. The method of claim 1, wherein the TNF-α is autocrine.

6. The method of claim 1, wherein the RIP3 is ectopically expressed.

7. The method of claim 1, wherein the smac mimetic is a smac small molecule dimer 3:

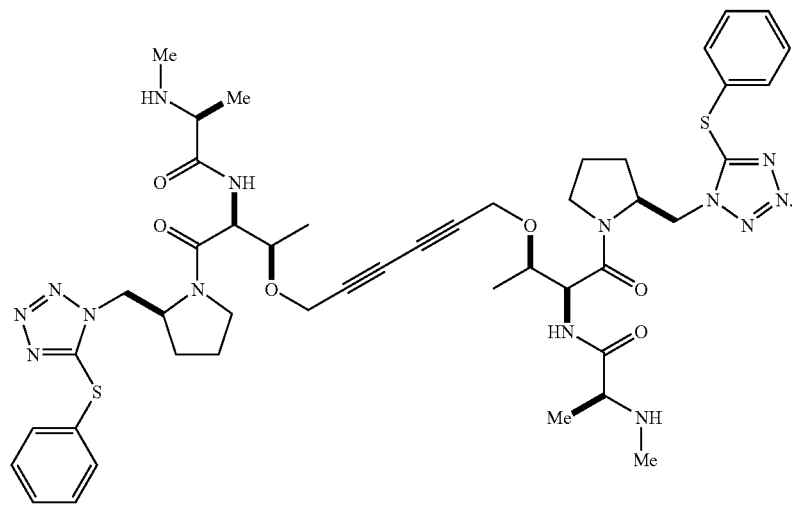
8. The method of claim 1, wherein the caspase-8 inhibitor is z-VAD or Q-VD-OPH.
* * * * *